United States Patent
Malamas

[11] Patent Number: 5,491,159
[45] Date of Patent: Feb. 13, 1996

[54] 2-(3,5-DI-TERT-BUTYL-4-HYDROXY-PHENYL)-OXAZOLES AS ANTI-ATHEROSCLEROTIC AGENTS

[75] Inventor: Michael S. Malamas, Jamison, Pa.

[73] Assignee: American Home Products Corporation, Madison, N.J.

[21] Appl. No.: 298,519

[22] Filed: Aug. 30, 1994

[51] Int. Cl.$^6$ .................................................. A61K 31/42
[52] U.S. Cl. ........................................... 514/374; 548/235
[58] Field of Search .............................. 548/235; 514/374

[56] References Cited

U.S. PATENT DOCUMENTS

| | | | |
|---|---|---|---|
| 4,636,516 | 1/1987 | Kubo et al. | 548/235 |
| 5,344,925 | 9/1994 | Goulet | 540/456 |
| 5,428,048 | 6/1995 | Malamas et al. | 548/235 |

FOREIGN PATENT DOCUMENTS 4117371  9/1990  Japan.

OTHER PUBLICATIONS

Steinberg, American Journal of Cardiology 57, 16H–21H (Jun. 27, 1986).
Reaven et al., Arteriosclerosis and Thrombosis 12(3), 318–324 (1992).
Carew et al., Proc. Natl. Acad. Sci. USA 84, 7725–7729 (1987).

Primary Examiner—Donald G. Daus
Attorney, Agent, or Firm—Robert F. Boswell, Jr.

[57] ABSTRACT

The earliest lesion of atherosclerosis is development of the fatty streak lesions which contain lipid-laden macrophages and lipid-laden smooth muscle cells. Macrophages do not take up native low density lipoprotein (LDL) but do take up modified, i.e., acetylated LDL or oxidized LDL via acetyl-LDL or "scavenger" receptors to form the foam cells of atherosclerotic plaque. Arterial smooth muscle cells generate superoxide and oxidize LDL in the presence of micromolar concentrations of $Cu^{+2}$ or $Fe^{+2}$. The way LDL can be modified by endothelial cells can be mimicked in vitro by incubation of the lipoprotein in the presence of $CuCl_2$. The compounds of this invention inhibit copper mediated oxidation of LDL in vitro and are thus useful in the prophylaxis and treatment of clinical conditions for which inhibition of the oxidative modification of lipids is indicated, for example, atherosclerosis. The compounds of this invention are represented by the formula 1 below

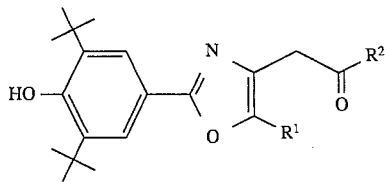

wherein:

$R^1$ is hydrogen, $C_1$–$C_6$ alkyl, phenyl or naphthyl;
$R^2$ is OH, $NH_2$, $OR^3$, or $NHCO_2R^4$ wherein
$R^3$ and $R^4$ are independently selected from $C_1$–$C_6$ alkyl, phenyl or naphthyl; or a pharmaceutically acceptable salt thereof.

11 Claims, No Drawings

2-(3,5-DI-TERT-BUTYL-4-HYDROXY-PHENYL)-OXAZOLES AS ANTI-ATHEROSCLEROTIC AGENTS

FIELD OF INVENTION

The present invention relates to the use of certain 2-[3,5-(di-tert-butyl)-4-hydroxy-phenyl]-oxazole compounds for the prophylaxis and treatment of clinical conditions for which inhibition of the oxidative modification of lipids is indicated, for example, atherosclerosis. The present compounds have the ability to scavenge peroxyl radicals implicated in the oxidation of low density lipoprotein and thus may be used as antiatherosclerotic agents.

BACKGROUND OF THE INVENTION

Atherosclerosis, the underlying disease implicated in myocardial infarction and strokes, is a complex pathologic process involving the intimal layer of the arteries. The earliest lesion of atherosclerosis is development of the fatty streak lesions which contain lipid-laden macrophages and lipid-laden smooth muscle cells. Macrophages do not take up native low density lipoprotein (LDL) but do take up modified, i.e., acetylated LDL or oxidized LDL via acetyl-LDL or "scavenger" receptors to form the foam cells of atherosclerotic plaque. Free radial oxidation, i.e., lipid peroxidation, has been shown to be involved in the alteration of LDL by endothelial cells. Arterial smooth muscle cells generate superoxide and oxidize LDL in the presence of micromolar concentrations of $Cu^{+2}$ or $Fe^{+2}$. The way LDL can be modified by endothelial cells can be mimicked in vitro by incubation of the lipoprotein in the presence of $CuCl_2$. Probucol, an antihyperlipidemic agent, also inhibits both cell mediated and $Cu^{+2}$ mediated oxidative modification of LDL, and was shown to inhibit the formation of atherosclerotic lesions in WHHL rabbits [Reaven et al., *Arteriosclerosis and Thrombosis* 12(3),318–324 (1992), Steinberg, *The Amer. J. of Cardiology* 57, 16H–21H (1986), Carew, Schwenke and Steinberg, *Proc. Natl. Acad. Sci.* 84, 7725–7729 (1987) and Nagano et al., *Arteriosclerosis* 9 (4), 453–461 (1989)]. Thus in vitro inhibition of $Cu^{+2}$ catalyzed oxidation of LDL is indicative of antiatherosclerotic utility.

The published unexamined Japanese patent application 4,117,341 discloses compounds of the formula:

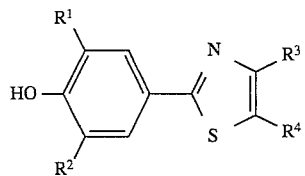

wherein $R^1$ and $R^2$ are lower alkyl and $R^3$ and $R^4$ are hydrogen, carbonyl, carboxy, lower (halo)alkyl, lower alkoxycarbonyl, lower alkoxycarbonylalkyl, lower hydroxyalkyl, phenylthio, phenyl optionally substituted with 1–3 substituents selected from OH, halogen, lower alkyl, and lower alkoxy, 4-$R^5$-piperazinyl-A- where $R^5$ is lowerhydroxyalkyl, phenyl optionally substituted with 1–3 substituents selected from halogen, lower hydroxyalkyl, lower fluoroalkyl and lower alkoxy and A is carbonyl or loweralkylene or $R^3$ and $R^4$ together forms an alkylene chain. These thiazoles, some of which are similar to the oxazole compounds of this invention, are disclosed to have antiinflammatory, antirheumatic, and ischaemic re-perfusing disturbance ameliorating action.

SUMMARY OF INVENTION

The compounds useful in the methods and pharmaceutical compositions of this invention are represented by Formula I below

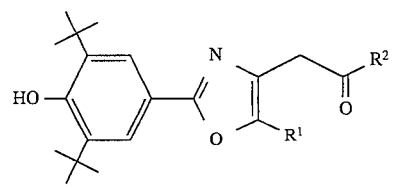

wherein:

$R^1$ is hydrogen, $C_1$–$C_6$ alkyl, phenyl or naphthyl;

$R^2$ is OH, $NH_2$, $OR^3$, or $NHCO_2R^4$ wherein $R^3$ and $R^4$ are independently selected from $C_1$–$C_6$ alkyl, phenyl or naphthyl; or a pharmaceutically acceptable salt thereof.

In the above definitions of variable terms, $C_1$–$C_6$ alkyl includes straight and branched chain alkyl groups and naphthyl includes 1-naphthyl and 2-naphthyl.

The term "pharmaceutically acceptable salt" means a salt formed by treating a Formula I compound with a pharmaceutically acceptable base such as an alkali metal or alkaline earth hydroxide or, when $R^2$ is —OH, ammonium hydroxide.

The oxazole compounds of this invention inhibit in vitro copper-induced peroxidation of LDL in procedures described hereinafter and thus would be useful in the treatment or prevention of atherosclerosis.

DETAILED DESCRIPTION OF THE INVENTION

The compounds of the present invention can be prepared according to the following synthetic scheme. Still other synthetic methods may be apparent to those skilled in the art.

Synthetic Scheme

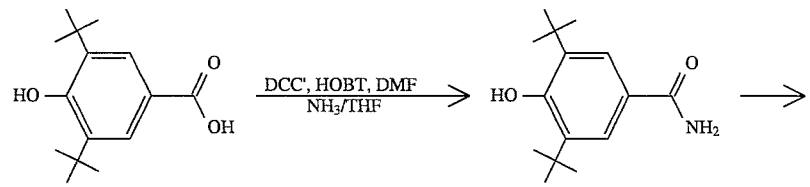

-continued
Synthetic Scheme

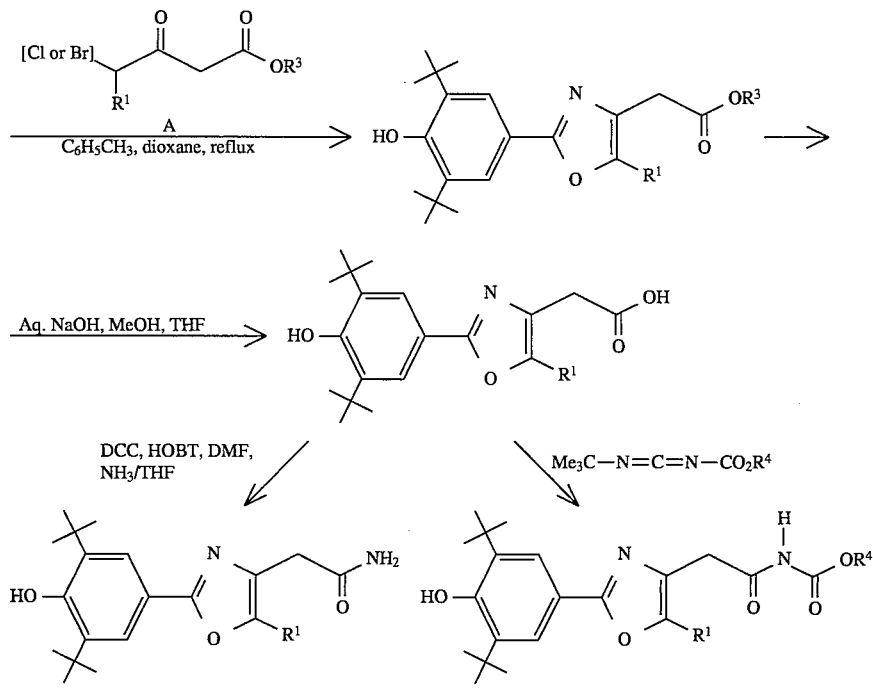

In the above scheme the variable terms $R^1$, $R^2$, $R^3$ and $R^4$ are as defined previously. The starting materials represented by the formula A are either commercially available or can be obtained by known methods conventional in the art, for example, according to Tetrahedron 1973, 29, 4251–4258.

The synthetic procedures illustrated above are exemplified in the following specific examples. These examples are included for illustrative purposes only and are not to be construed as limiting this disclosure in any way. Formula I compounds or pharmaceutically acceptable salts thereof may be isolated as hydrated or solvated solids and are considered to be biologically equivalent to the non-hydrated or nor-solvated form when the percent active compound of the total is considered.

EXAMPLE 1

[2-(3,5-di-tert-butyl-4-hydroxyphenyl)-5-methyloxazol-4-yl]-acetic acid methyl ester Step a) 3,5-di-tert-butyl-4-hydroxybenzamide A mixture of 3,5-di-tert-butyl-4-hydroxybenzoic acid (30.0 g, 120.0 mmol), 1-(3-dimethylaminopropyl)-3-ethylcarbodiimide hydrochloride (25.3 g, 132.0 mmol), 1-hydroxybenzotriazole hydrate (21.08 g, 156.0 mmol) and N,N-dimethylformamide (200 mL) was stirred at room temperature for 2 hours. Then, a freshly prepared saturated $NH_3$/THF solution (200 mL) was added slowly. After 20 minutes the reaction mixture was poured into water and acidified with HCl (2N). The precipitated solid was filtered and dried to give a white solid (24.5 g, 81% yield), m.p. 252°–254° C.

Analysis for: $C_{15}H_{23}NO_2$ Calc'd: C, 72.25; H, 9.30; N, 5.62 Found: C, 72.29, H, 9.27; N, 5.72

Step b) [2-(3,5-di-tert-butyl-4-hydroxyphenyl)-5-methyloxazol-4-yl]-acetic acid methyl ester A mixture of 3,5-di-tert-butyl-4-hydroxybenzamide (16.0 g, 64.3 mmol), 4-bromo-3-oxopentanoic acid methyl ester (18.6 g, 64.26 mmol), dioxane (60 mL), and toluene (600 mL) was refluxed for 5 days with continuous water removal (Dean Stark trap). Then, the volatiles were removed in vacuo and the residue was purified by flash chromatography on silica gel (eluting solvent: hexane/EtOAc 3/1) to give a brown viscous oil (11.2 g). Crystallization of the brown oil from ethyl ether (after cooling to 0° C.) gave a white solid (9.2 g, 40% yield), m.p. 121°–123° C.

Analysis for: $C_{21}H_{29}NO_4$ Calc'd: C, 70.17; H, 8.13; N, 3.90 Found: C, 70.49, H, 8.17; N, 3.80

EXAMPLE 2

[2-(3,5-di-tert-butyl-4-hydroxyphenyl)-5-methyloxazol-4-yl]-acetic acid

Sodium hydroxide (2N, 5.0 mL, 10.0 mmol) was added to a solution of [2-(3,5-di-tert-butyl-4-hydroxyphenyl)-5-methyloxazol-4-yl]-acetic acid methyl ester (1.5 g, 4.18 mmol), MeOH (15 mL), and THF (15 mL). After stirring for 1 hour, the mixture was poured into water, acidified with HCl (2N) and extracted with EtOAc. The organic extracts were dried over $MgSO_4$. Evaporation and crystallization from acetone/ethyl ether/hexane gave a white solid (1.25 g, 87% yield), m.p. 205°–206° C.

Analysis for: $C_{20}H_{27}NO_4$ Calc'd: C, 69.54; H, 7.88; N, 4.05 Found: C, 69.58, H, 7.97; N, 3.98

EXAMPLE 3

[2-(3,5-di-tert-butyl-4-hydroxyphenyl)-5-methyloxazol-4-yl]-acetic acid ethyl ester A mixture of [2-(3,5-di-tert-butyl-4-hydroxyphenyl)-5-methyloxazol-4-yl]-acetic acid (1.5 g, 4.35 mmol), EtOH (50 mL), and concentrated sulfuric acid (0.5 mL) was refluxed for 10 hours. The mixture poured into water, and extracted with EtOAc. The organic extracts were dried over $MgSO_4$. Evaporation and crystallization from ethyl ether/hexane gave a light brown solid (1.35 g, 83% yield), m.p. 103°–105° C.

Analysis for: $C_{22}H_{31}NO_4$ Calc'd: C, 70.75; H, 8.36; N, 3.75 Found: C, 71.04, H, 8.50; N, 3.76

EXAMPLE 4

[2-(3,5-di-tert-butyl-4-hydroxyphenyl)-oxazol-4-yl]-acetic acid methyl ester

A mixture of 3,5-di-tert-butyl-4-hydroxybenzamide (5.0 g, 20.0 mmol), methyl 4-chloroacetoacetate (3.01 g, 20.0 mmol), dioxane (30 mL), and toluene (300 mL) was refluxed for 5 days, with continuous water removal (Dean Stark trap). The volatiles were removed in vacuo and the residue was purified by flash chromatography on silica gel (eluting solvent: hexane/EtOAc 3/1) to give a brown viscous oil (3.2 g). Crystallization of the brown oil from ethyl ether (after cooling to 0° C.) gave a white solid (2.6 g, 38% yield), m.p. 126°–128° C.

Analysis for: $C_{20}H_{27}NO_4$ Calc'd: C, 69.56; H, 7.83; N, 4.06 Found: C, 69.26, H, 7.82; N, 3.91

EXAMPLE 5

{2-[2-(3,5-di-tert-butyl-4-hydroxyphenyl)-5-methyloxazol-4-yl]acetyl}carbamic acid methyl ester A mixture of [2-(3,5-di-tert-butyl-4-hydroxyphenyl)-5-methyloxazol-4-yl]-acetic acid (2.0 g, 5.8 mmol), N-methoxy-N'-tert-butylcarbodiimide (0.9 g, 5.8 mmol) prepared according to Bull. Chem. Soc. Japan 45, 3607–3611 (1972) and THF (20 mL) was refluxed for 6 hours. The volatiles were removed in vacuo, and the residue was purified by flash chromatography on acid washed silica gel (5% $H_3PO_4$ in MeOH), eluting solvent: hexane/EtOAc 3/1, to give an off-white solid (2.2 g, 94% yield), m.p. 125°–127° C.

Analysis for: $C_{22}H_{30}N_2O_5$ Calc'd: C, 65.65; H, 7.51; N, 6.96 Found: C, 65.71, H, 7.70; N, 6.86

Inhibition of Copper Ion Mediated Oxidation of Low Density Lipoprotein

In this in vitro assay, the inhibition of $Cu^{+2}$ mediated oxidation of rabbit or monkey LDL by an invention compound is determined spectrophotometrically. Oxidation of LDL results in the formation of LDL-diene which absorbs light at 532 nm. Inhibition of oxidation of LDL leads to a decrease in absorbance at 532 nm.

Rabbit or monkey LDL is prepared according to the procedures of Havel, Eder and Gragdon, "The Distribution and Chemical Composition of Ultracentrifugally Separated Lipoproteins in Human Serum,: J. Clin. Invest. 34, 1345–1353 (1955) and Parhtasarathy, Wieland and Steriberg, "A Role for Endothelial Cell Lipoxygenase in the Oxidative Modification of Low Density Lipoprotein," Proc. Natl. Acad. Sci. USA 86, 1046–1050 (1989). Test compound solutions are prepared by dissolving the invention compounds in ethanol at concentrations up to 248 µM. The medium used is Dulbecco's phosphate buffered saline containing 0.5 mg/ml bovine serum albumin. For standards, 0 to 10 µl of an aqueous solution of 1,1,3,3-tetraethoxypropane (1 µmol/ml $H_2O$) in 4.1 ml of medium is used.

Test compound solution (100 µl) is added to 4 ml of medium in incubation tubes. To each tube is added 10 µl of LDL solution and 25 µl of aqueous copper sulfate solution (1.32 mg/ml $H_2O$). The tubes are incubated at 37° C. for 90 minutes and the oxidation reaction quenched by addition of 1 ml of thiobarbituric acid solution (0.67% in 50% acetic acid). The tubes are heated at 90° C. for 1 hour, then chilled in an ice bath and the chromophore extracted into 2 ml of n-butanol. Absorbence is read at 532 nm and the results are reported as nmols of malondialdehyde equivalents.

Significant differences ($p<0.05$) are determined by the Dunnett T-test or by the Student-Newman Keuls Test for significant differences between means. The assay is conducted using several concentrations [I] of the inhibitor test compounds. The LDL solution concentrations at different experiments were either 1.5 mg/ml, 2.5 mg/ml or 10.3 mg/ml. The $IC_{50}$ is determined by non-linear regression, plotting log [I] vs. % inhibition. (Reference: K. Yagi, Biochemical Medicine 15, 212–216 (1976)). The results obtained with invention compounds are shown in Table I.

TABLE I

| In-Vitro Inhibition of Copper Mediated LDL Oxidation | |
|---|---|
| EXAMPLE NO. | $IC_{50}$ (µM) |
| 1 | 0.07 |
| 2 | 0.16 |
| 3 | 0.27 |
| 4 | 0.25 |
| 5 | 0.23 |
| probucol | 0.27 |

Pharmaceutical Composition and Administration

When the compounds of the invention are employed in the treatment of atherosclerosis, they can be formulated into oral dosage forms such as tablets, capsules and the like. The compound can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be administered parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day. The drug probucol is administered to humans in a daily dosage of from 250 mg to 1000 mg/day. Compounds of this invention appear to be equipotent to or more potent than probucol in the in-vitro assay and are thus contemplated to have a daily dosage range in adult humans of from 1 mg/day to 1000 mg/day.

What is claimed is:

1. A compound having the formula:

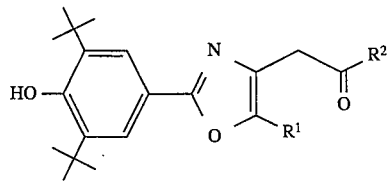

wherein:

$R^1$ is hydrogen, $C_1$–$C_6$ alkyl, phenyl or naphthyl;

$R^2$ is OH $NH_2$, $OR^3$, or $NHCO_2R^4$ wherein $R^3$ and $R^4$ are independently selected from $C_1$–$C_6$ alkyl, phenyl or naphthyl; or a pharmaceutically acceptable salt thereof.

2. A compound according to claim 1 which is [2-(3,5-di-tert- butyl-4-hydroxyphenyl)-5-methyloxazol-4-yl]-acetic acid methyl ester.

3. A compound according to claim 1 which is [2-(3,5-di-tert- butyl-4-hydroxyphenyl)-5-methyloxazol-4-yl]-acetic acid.

4. A compound according to claim 1 which is [2-(3,5-di-tert- butyl-4-hydroxyphenyl)-5-methyloxazol-4-yl]-acetic acid ethyl ester.

5. A compound according to claim 1 which is [2-(3,5-di-tert- butyl-4-hydroxyphenyl)-oxazol-4-yl]-acetic acid methyl ester.

6. A compound according to claim 1 which is {2-[2-(3,5-di-tert-butyl-4-hydroxyphenyl)-5-methyloxazol-4-yl]acetyl}carbamic acid methyl ester.

7. A method of inhibiting oxidative modification of low density lipoprotein which comprises administration to a mammal in need thereof a therapeutically effective amount of a compound having the formula:

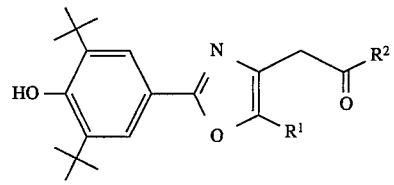

wherein:

$R^1$ is hydrogen, $C_1$–$C_6$ alkyl, phenyl or naphthyl;

$R^2$ is OH, $NH_2$, $OR^3$, or $NHCO_2R^4$ wherein $R^3$ and $R^4$ are independently selected from $C_1$–$C_6$ alkyl, phenyl or naphthyl; or a pharmaceutically acceptable salt thereof.

8. The method according to claim 7 wherein the therapeutically effective compound used is selected from the group consisting of:

[2-(3,5-di-tert-butyl-4-hydroxyphenyl)-5-methyloxazol-4yl]-acetic acid methyl ester,

[2-(3,5-di-tert-butyl-4-hydroxyphenyl)-5-methyloxazol-4-yl]-acetic acid,

[2-(3,5-di-tert-butyl-4-hydroxyphenyl)-5-methyloxazol-4-yl]-acetic acid ethyl ester,

[2-(3,5-di-tert-butyl-4-hydroxyphenyl)-oxazol-4-yl]-acetic acid methyl ester, and {2-[2-(3,5-di-tert-butyl-4-hydroxyphenyl)-5-methyloxazol-4-yl]acetyl}carbamic acid methyl ester.

9. A method for treating atherosclerosis which comprises administration to a mammal in need thereof a therapeutically effective amount of a compound of the formula:

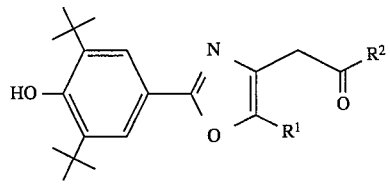

wherein:

$R^1$ is hydrogen, $C_1$–$C_6$ alkyl, phenyl or naphthyl;

$R^2$ is CH, $NH_2$, $OR^3$, or $NHCO_2R^4$ wherein $R^3$ and $R^4$ are independently selected from $C_1$–$C_6$ alkyl, phenyl or naphthyl; or a pharmaceutically acceptable salt thereof.

10. The method according to claim 9 wherein the compound used is selected from the group consisting of:

[2-(3,5-di-tert-butyl-4-hydroxyphenyl)-5-methyloxazol-4-yl]-acetic acid methyl ester,

[2-(3,5-di-tert-butyl-4-hydroxyphenyl)-5-methyloxazol-4-yl]-acetic acid,

[2-(3,5-di-tert-butyl-4-hydroxyphenyl)-5-methyloxazol-4-yl]-acetic acid ethyl ester,

[2-(3,5-di-tert-butyl-4-hydroxyphenyl)-oxazol-4-yl]-acetic acid methyl ester, and {2-[2-(3,5-di-tert-butyl-4-hydroxyphenyl)-5-methyloxazol-4-yl]acetyl}carbamic acid methyl ester.

11. A pharmaceutical composition which comprises a pharmaceutically acceptable carrier and a therapeutically effective amount of a compound of the formula:

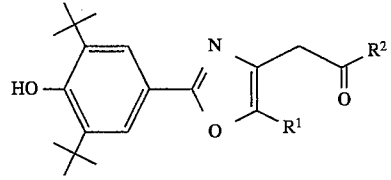

wherein:

$R^1$ is hydrogen, $C_1$–$C_6$ alkyl, phenyl or naphthyl;

$R^2$ is OH, $NH_2$, $OR^3$, or $NHCO_2R^4$ wherein $R^3$ and $R^4$ are independently selected from $C_1$–$C_6$ alkyl, phenyl or naphthyl; or a pharmaceutically acceptable salt thereof.

* * * * *